United States Patent [19]

Truesdale, Jr.

[11] Patent Number: 4,990,135
[45] Date of Patent: Feb. 5, 1991

[54] INOCULATOR AND NEEDLE THEREFOR

[76] Inventor: R. Grant Truesdale, Jr., 115 Woodburn Rd., Raleigh, N.C. 27605

[21] Appl. No.: 399,847

[22] Filed: Aug. 29, 1989

[51] Int. Cl.⁵ ............................................. A61B 17/20
[52] U.S. Cl. ......................................... 604/47; 604/196
[58] Field of Search ........................... 604/47, 195–196, 604/239, 272, 274

[56] References Cited

U.S. PATENT DOCUMENTS

| | | |
|---|---|---|
| 229,518 | 12/1973 | Bujan . |
| 583,427 | 5/1897 | Bomgardner . |
| 648,858 | 5/1900 | Dolge . |
| 724,522 | 4/1903 | Thomas . |
| 2,268,321 | 11/1940 | Flynn . |
| 2,512,882 | 6/1950 | Truesdale ............................ 604/47 |
| 2,560,162 | 2/1950 | Ferguson . |
| 2,601,580 | 6/1952 | Yanus . |
| 2,617,418 | 12/1950 | Del Pico . |
| 2,634,726 | 1/1952 | Hanson . |
| 2,748,769 | 2/1953 | Huber . |
| 2,989,053 | 1/1956 | Hamilton . |
| 3,064,651 | 5/1959 | Henderson . |
| 3,067,742 | 5/1960 | Linke et al. . |
| 3,194,237 | 10/1962 | Rubin . |
| 3,448,740 | 6/1969 | Figge . |
| 4,068,661 | 1/1978 | Hennings . |
| 4,125,113 | 11/1978 | Morman et al. . |
| 4,413,993 | 11/1983 | Guttman . |
| 4,542,749 | 9/1985 | Caselgrandi et al. . |
| 4,565,545 | 1/1986 | Suzuki . |
| 4,666,438 | 5/1987 | Raulerson . |
| 4,702,260 | 10/1987 | Wang . |

FOREIGN PATENT DOCUMENTS

| | | | |
|---|---|---|---|
| 3020926 | 12/1981 | Denmark ............................ | 604/274 |
| 904716 | 2/1982 | U.S.S.R. . | |

Primary Examiner—Stephen C. Pellegrino
Assistant Examiner—Michael Rafa
Attorney, Agent, or Firm—Rosenthal & Putterman

[57] ABSTRACT

A serum inoculator for inoculating birds is disclosed. The inoculator includes a reservoir and a reciprocable needle having a portion movable into and out of the reservoir for insertion in and removal from the bird to be inoculated. The needle includes in that portion which enters and exits from the reservoir, an elongate diametric slot defining a side opening in each side of the needle. The slot includes flared sides and a projection extending into the slot at each end thereof and being adapted to positively attract and hold a predetermined measured serum dose for a single inoculation. A wiper fixed in position at the dispensing end of the reservoir for removing from the needle the serum other than that contained in the elongate diametric slot. A plunger is provided for imparting reciprocating strokes to the needle for drawing the elongate diametric slot into the reservoir and for charging it with serum and to project it therefrom to an exposed position for inoculating use.

19 Claims, 2 Drawing Sheets

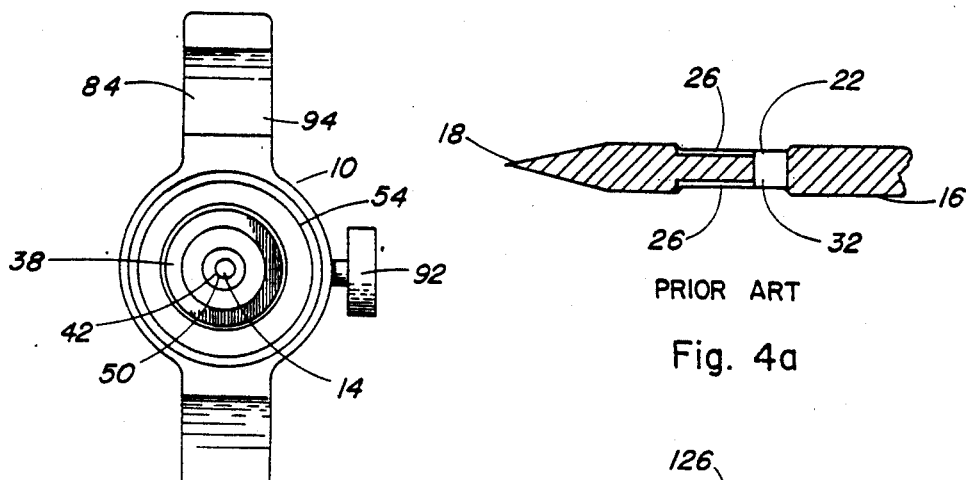
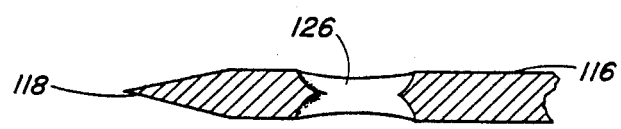
Fig. 3   Fig. 4b
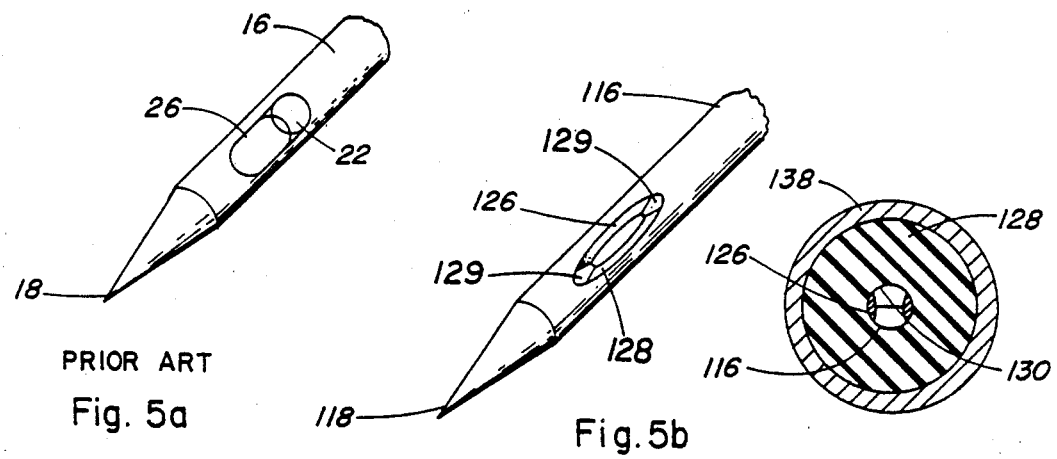
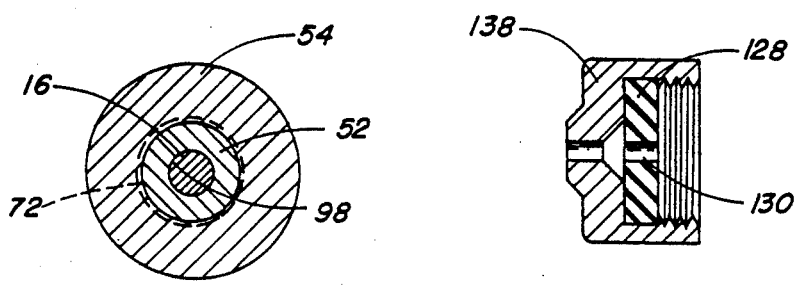
Fig. 7   Fig. 8

4,990,135

INOCULATOR AND NEEDLE THEREFOR

FIELD OF THE INVENTION

This invention relates generally to the field of inoculators and more particularly to the field of inoculators used to vaccinate poultry and other farm animals.

BACKGROUND OF THE INVENTION

It is well known to inoculate poultry against contagious diseases such as chicken pox, laryngo-tracheitis, Newcastle disease, etc.

For example, one method of inoculating poultry is to dip a needle or a knife into a bottle of serum in an open crock or other holder and then to "stick" the coated needle into the bird. A portion of the serum frequently drops off from the penetrating instrument and in time this amounts to a substantial loss of serum. In addition, this method provides no accurate measurement of the amount of serum introduced into the bird. The needles or knives are not wiped off between inoculation of birds and, it is almost impossible for a single operator to inoculate a bird himself. At least one hand is needed to hold the bird, and it is difficult for the inoculating party to hold the bird with one hand and to dip the needle or pen knife into the bowl of serum with the other hand while trying to hold the bird. There is also a possibility of the moving bird knocking over the container, losing valuable serum.

In order to inoculate the bird properly, the inoculating party must be seated and, therefore, to achieve efficient inoculation, one sitting party is needed to inoculate the birds and another party is needed to catch the birds and hand them to him, thereby increasing the cost of inoculation.

In response to the above-noted difficulties in inoculating poultry, the inoculators disclosed in U.S. Pat. No. 2,512,882 to Truesdale and U.S. Pat. No. 2,617,918 to Del Pico were conceived.

The Truesdale inoculator comprises a reservoir for the serum. A reciprocable needle extends through the reservoir along its axis. The needle has a pointed end adapted to be projected into the bird to be inoculated. The needle is solid except for an indentation that carries a predetermined dose of serum. Means for reciprocating the needle are provided so that as the indentation enters the reservoir on one stroke, it is charged with the serum, and on the other stroke is pushed out of the reservoir into an inoculating position.

The Truesdale inoculator described above advanced the art of poultry inoculation as it was possible for inoculation of a bird to be accomplished by a single individual working alone. In addition, the serum was contained in a closed reservoir which eliminated the possibility of spillage and furthermore, a precise dose was delivered to the bird. While the Truesdale inoculator was truly an advancement in the art, and is still widely in use today, it too has its deficiencies.

In the poultry industry, when a bird is properly inoculated and resistance to the disease inoculated against develops, this is referred to as a "take". About twenty percent of the time, using the Truesdale inoculator an air lock develops and serum fails to be transferred from the reservoir to the indentation in the needle. Consequently only about 80 percent of the birds inoculated receive a "take" and while this is a vast improvement over the prior art, the percentages could still be improved It is, therefore, an object of the present invention to provide a poultry inoculator which improves the "take" without sacrificing any of the other advantages found in the Truesdale inoculator.

It is another object of the present invention to provide a poultry inoculator which will reliably deliver a predetermined amount of serum to the bird It is still further object of the present invention to provide a poultry inoculator which will prevent the serum from coming into contact with the operator.

It is yet another object of the present invention to provide a poultry inoculator which prevents the serum from becoming contaminated with air, dust and dirt, thus maintaining its strength.

SUMMARY OF THE INVENTION

The foregoing objects are accomplished in accordance with the present invention by providing a serum inoculator of the type used to inoculate birds and the like The inoculator comprises a serum holding reservoir having a dispensing hole. A needle extends through the reservoir along the axis of the inoculator and is reciprocable in the reservoir from a closed position with its pointed end substantially contained within the hole to an inoculating position with its end projecting an inoculating distance beyond the hole. The needle includes a measured serum dose receiving means at a closely spaced distance from the pointed end. The measured dose receiving means includes an elongated slot having a side opening that is flared about a substantial portion of its perimeter. The slot also includes a projection means projecting into the slot. The flared edges and the projection means act to attract therein a predetermined measured serum dose when the serum dose receiving means is in contact with said reservoir and for releasing the serum into a bird when the serum dose receiving means is inserted therein The inoculator includes fixed wiper means in the reservoir adjacent the dispensing hole forming with the pointed end of the needle when the needle is in the closed position a seal for sealing serum within the reservoir. The means for wiping the needle on each inoculating movement thereof wipes the needle but allows a measured dose to remain within the measured dose receiving means. The inoculator also includes a plunger connected to the needle that extends along the axis of the inoculator to a position to be manually activated to move the needle from a closed to an inoculating position. A spring means is coiled about the needle and acts on the plunger to return the needle from its inoculating position to its closed position.

BRIEF DESCRIPTION OF THE DRAWINGS

Some of the features and advantages of the invention having been briefly stated while others will appear from the detailed description which follows, when taken in connection with the accompanying drawings, in which—

FIG. 3 is an end view looking from the left in FIG. 2.

FIG. 4a is an enlarged medial view of the needle of the prior art.

FIG. 4b is an enlarged medial view of the needle of the present invention.

FIG. 5a is a perspective view of the needle of the prior art.

FIG. 5b is a perspective view of the needle of the present invention.

FIG. 6 is a sectional view taken along line 6—6 of FIG. 2 showing the inoculating end of the needle of the present invention.

FIG. 7 is a sectional view taken along line 7—7 of FIG. 2.

FIG. 8 is a sectional view of the sealing element and wiper of the present invention.

DETAILED DESCRIPTION OF THE ILLUSTRATED EMBODIMENT

Figure 1:
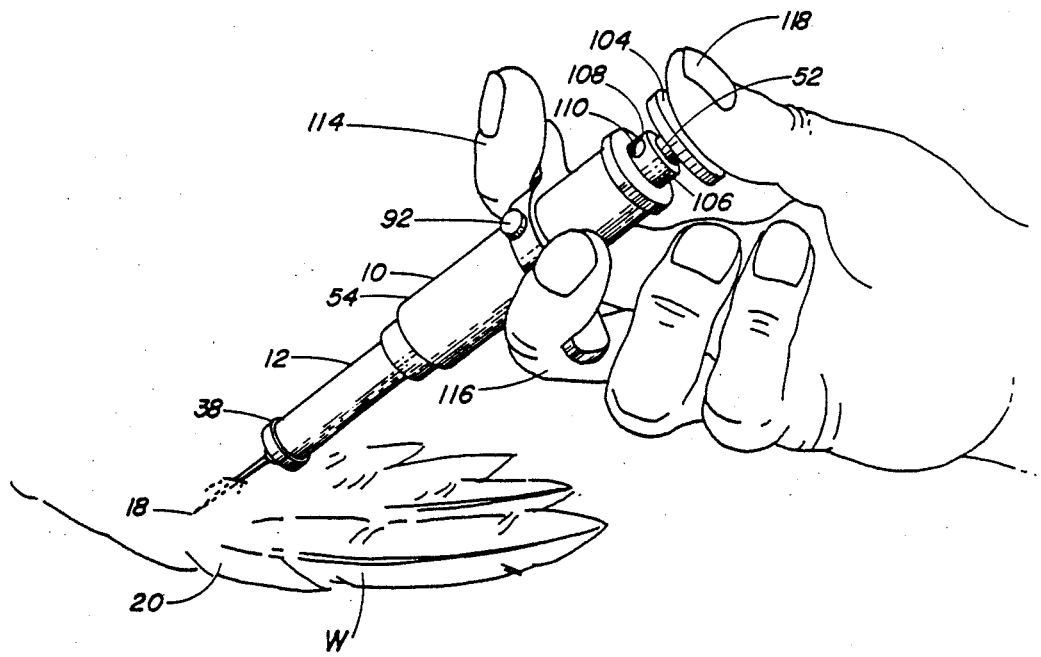
FIG. 1 is a perspective view of the poultry inoculator of the present invention being used to inoculate the wing of a fowl with the needle in the inoculating position.

While the present invention will be described more fully hereinafter with reference to the accompanying drawings, in which a particular embodiment is shown, it is to be understood at the outset that persons skilled in the art may modify the invention herein described while still achieving the favorable results of this invention. Accordingly, the description which follows is to be understood as a broad teaching disclosure directed to persons of skill in the appropriate arts and not as limiting upon the present invention.

In the drawings, wherein like characters of reference generally indicate like parts throughout, 10 indicates a serum inoculator constructed in accordance with the invention.

Figure 2:
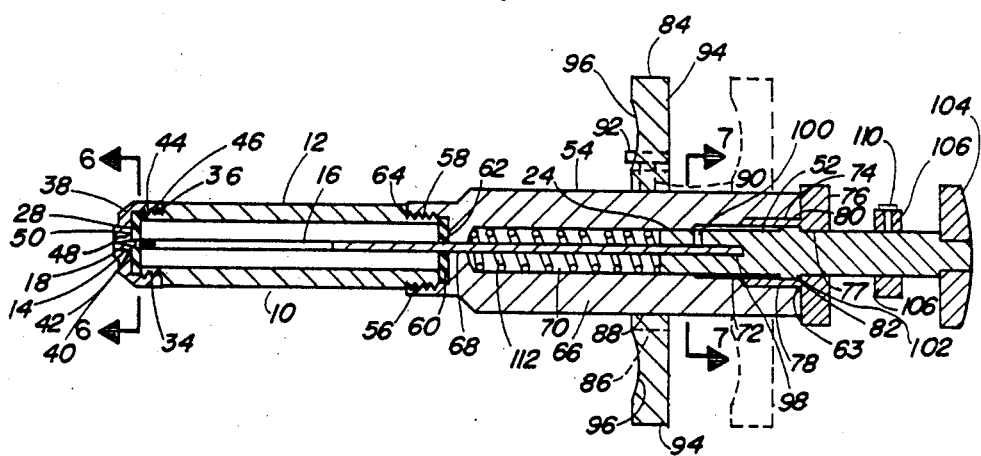
FIG. 2 is a medial view taken through the poultry inoculator of the present invention and showing the needle retracted to the closed position.

In the broader aspects of the invention the serum inoculator includes a preferably transparent serum holding reservoir 12 having a dispensing hole 14 therein, preferably in the lower end thereof, and a needle 16 extending through the reservoir and capable of being reciprocated from a closed position with its pointed end 18 substantially contained in the hole 14 as shown in FIG. 2 to an inoculating position with its pointed end 18 projecting an inoculating distance beyond the hole into the wing W of the bird as shown in FIG. 1.

The needle 16 has a measured dose receiving means or needle eye 126 that includes an elongated slot having a side opening that is flared about a substantial portion of its outer perimeter. The measured dose receiving means 126 is adapted to attract therein a predetermined measured serum dose when the dose receiving means is in contact with the reservoir and for releasing the serum into a bird when the pointed end of the needle is inserted therein In the preferred embodiment, shown in FIGS. 4b, 5b and 6 the measured dose receiving means 126 comprises a diametric elongated slot that extends through the needle and defines one side opening on each side of the needle. Each of the openings includes flared edges 128 about its respective perimeter. In addition, located at each end of the slot is a pointed projection means or projection 129 which extends therein. The slot geometry defined by the combination of the flared edges 128 and the projections 129 results in an inoculator which positively attracts the serum from the reservoir 12 and is, therefore, available for delivery to the bird with reliability approaching 100 percent.

The improved reliability of the inoculator is derived from the changes in needle geometry from that of the prior art as shown in FIGS. 4a and 5a to the improved geometry shown in FIGS. 4b, 5b and 6. It is believed that the serum stays attached within the needle eye due to a number of factors. First, molecular adhesion takes place due to the unique geometry of the needle eye where the projections 129 at each end and the flared edges 128 grip and hold the serum in place. Second, internal molecular friction within the serum occurs across the needle eye 126 "binding" the fluid together. Next, once the serum is outside the inoculator, tension on the fluid surface occurs due to the atmospheric pressure and fluid molecules binding tangent to the fluid surface, thus, holding the fluid in the needle eye 126 Lastly, as the needle eye 126 penetrates the skin of the bird, the surface tension is broken, which allows the serum fluid to flow from the needle eye 126 into the bird by capillary action.

From the foregoing it will be seen that the improved needle eye geometry causes the serum to be attracted and held within the needle eye 126 as described above. However, it will be noted that the needle eye 126 may take various shapes, such as circular, ovoid, etc., and may even be an indentation rather than a diametric opening such as has been described herein. In addition, depending on the geometry selected, the edges thereof may be completely or partially flared and one or more projections may or may not be required to adequately grip and hold the serum in place. Thus, while other needle eye geometries have not specifically been discussed, they are intended to be within the scope of this invention.

A means 28 is provided in the reservoir forming with the end of the needle when the needle is in a closed position, a seal for sealing serum within the reservoir and serving to wipe the needle on each inoculating movement thereof, except the measured dose contained within the measured dose receiving means 126.

In the preferred embodiment, the means 28 is an annular sealing element mounted within the lower end of said reservoir 12 adjacent the hole 14, having a central hole 30 with its edge adapted to abut the surface of the needle 16 as it passes through the hole to wipe all serum from the needle on each inoculating movement thereof except a measured dose of the serum contained within the diametric needle eye 126. It will also be noted that the element 28 functions not only as a wiper to wipe all excess serum off the needle as it is being advanced from the reservoir, but also operates to wipe all material from the end of the needle, including any foreign or diseased matter taken from the fowl inoculated as it is being retracted within the reservoir 12.

The serum holding reservoir 12 has the reduced nipple forming lower end 34, preferably externally threaded as at 36. The annular sealing element 28 is clamped between the annular edge of this nipple end and a retaining cap 38 which has a skirt 44 internally threaded at 46 to screw onto the threads 36 of the reservoir. A wall 40 of the cap 38 has a central hole 42 from the edge of which the wall 40 diverges on the inside of the cap to provide a sort of conical seat 50.

The wiping washer or annular sealing element 28, as shown in FIG. 8, is provided with a conical mound 48 projecting outwardly therefrom, having the needle hole 30 therein, for engaging the conical seat 50 on the retaining cap 38.

The serum inoculator 10 comprises a cylinder 54 and the means to reciprocate the needle 16 within the cylindrical reservoir 12 comprises a plunger 52 reciprocable in the piston cylinder 54. The lower end of the piston cylinder 54 has an internally threaded socket 56 and the upper end of the cylindrical reservoir 12 has an externally threaded nipple 58 threaded within said socket 56 and an annular resilient washer 60 having a central needle hole 62 is clamped by the reservoir nipple 58 against the base of said socket 56.

The upper cylinder 54, plunger 52 and needle 16 are made of suitable metal. While the reservoir 12 may also be made out of suitable metal, it is preferably made out of a suitable transparent substance such as Lucite (methyl methacrylate) or glass. The lower sealing washer 28 may also be made of brass, if desired, but is preferably made of resilient Teflon (tetra-fluor ethylene resin), resilient neoprene or any other suitable washer material. The lower washer 28 may also be made of resilient material such as neoprene, rubber, or otherwise.

As stated, the plunger 52 and the cylinder 54 in which it reciprocates are constructed of simple parts which may be readily machined on a lathe or automatic screw machine or otherwise The cylinder 54 preferably comprises the cylindrical barrel, cylindrical externally throughout the length thereof, having an open end 63, an open end 64 and a relatively thick wall 66. The cylinder 54 is provided with a central hole having the enlarged socket forming lower portion 56, a portion 68 of a diameter substantially that of the inoculating needle 16, an elongated cylinder forming bore 70 of relatively large diameter, another portion 72 of slightly larger diameter and an internally threaded socket forming portion 74 of still greater diameter in the open end 63 thereof.

A guide nut 76 having a shank 78 externally threaded as at 36 threaded within said socket 74 and a central plunger hole 82 of the diameter of the said cylindrical hole portion 72 is provided.

For the purpose to be described, a finger grip 84 having a hub 86 with the hole 88 therein to make said hub 86 longitudinally adjustable throughout the length of the barrel 54 is provided. The hub 86 includes a radial set screw adjusting hole 88 therein to receive the locking set screw 92. The finger grip 84 has diametrically opposed arms 94 suitably grooved on one side as at 96 to receive the operator's fingers therein as shown in FIG. 1.

It is apparent that with this construction the finger grip may be longitudinally adjustable on said barrel 54.

The cylindrical plunger 52 of substantially uniform diameter, having a portion thereof reciprocable within the said cylinder 54 having the central hole 98 therein to receive one end of the needle 18, and having a threaded radial hole 100 for a set screw whereby the needle is secured to the plunger. There is a stop collar 102 preferably formed integrally on the plunger 52 having a diameter approximating that of the bore 72 and of the hole 82 in the guide nut 76 but larger than the hole 77 in said nut. Thus the collar 102 is adapted to abut the lower surface of the guide nut 76 when in raised position. The plunger 52 terminates in a thumb operated button 104 at the outer end thereof spaced above the guide nut 76 a greater distance than that of the desired plunger movement. The stop collar 106 is adjustably mounted on the plunger 52 between the guide nut 76 and button 104. The stop collar 106 is provided with the radial hole 108 therein to receive the set screw 110 for longitudinal adjustment thereof to adjustably limit the extent to which the needle may be pushed out from the discharge end of the reservoir 12.

A coil spring 112 is provided having one end abutting the annular seat at the elongated cylinder bore portion 70 and having its other end abutting the inner end of the plunger to urge said plunger normally to its retracted position with the end 18 of the needle closing the hole 14 in the reservoir 12. In all positions, therefore, the elongated needle extends through the coil spring 112, barrel needle bore portion 68, reservoir 12, reservoir wiping washer 28 and cap 38.

In use, the reservoir 12 is filled with the desired amount of serum, normally an entire bottle full as sold b the manufacturer, enough for a multiplicity of doses. When it is desired to use the device, the forefinger 114 and middle finger 118 may have the ends thereof inserted within the grooves 96 in the arms 94 of the finger grip 84 and the thumb 118 pressed against the thumb button 104 in such a manner as to urge the point 18 of the needle an inoculating distance from the reservoir. It is obvious that as the inoculating needle 10 is pushed outwardly the wiping washer 28 will function to wipe all excess serum from the needle as it passes through the hole 30 to without the reservoir, the elongated mound 48 increasing the depth of the hole 30 to insure a positive wiping action. The point of the needle 18 then may be inserted up to the depth of the hole 22 within the leg or wing of the fowl W as shown in FIG. 1. As the needle 16 is withdrawn from the fowl, the thumb may be removed and the spring 112 will force the plunger 52 outwardly carrying the needle 16 with it so that the surface of the needle which has been outside the reservoir is also wiped by the washer 28 as the point 18 is retracted within the reservoir 12 so as to fill the hole 14 in the reservoir, it being obvious that this wipes any diseased tissue which may remain on the projecting end of the needle. It is thus to be seen that an additional benefit derived by this construction is that a minimum amount of serum is used for each inoculation and that no serum is lost except that which is actually used. In addition, the serum is kept in a safe close container free from dust, dirt and contamination at all times, and that the needle is carefully wiped of all possible contaminating matter prior to being withdrawn into the reservoir, so that its point 18 again fills the hole 14 in the reservoir.

It is also obvious that, as shown in FIG. 1, the needle may be readily manipulated by a single operator with one hand, while his other hand holds the chicken against its perch.

It is understood that my invention is not limited to the specific embodiment shown and that various deviations may be made therefrom without departing from the spirit and scope of the appended claims.

That which is claimed is:

1. A serum inoculator of the type used to inoculate birds and the like against diseases and comprising:
   a serum holding reservoir having a dispensing hole;
   a needle extending through said reservoir along the axis of the inoculator and being reciprocable in said reservoir from a closed position with its pointed end substantially contained in said hole, to an inoculating position with its end projecting an inoculating distance beyond said hole;
   said needle having a measured serum dose receiving means at a closely spaced distance from said pointed end, said measured dose receiving means including an elongated slot having a side opening that is flared about a substantial portion of its outer perimeter and being adapted for attracting therein a predetermined measured serum dose when said dose receiving means is in contact with said reservoir and for releasing the serum into a bird when the pointed end of the needle is inserted therein;

fixed wiper means in said reservoir adjacent said dispensing hole forming with the pointed end of said needle when said needle is in closed position a seal for sealing serum within said reservoir;

said fixed wiper means for wiping said needle on each inoculating movement thereof except that of a measured dose contained within said measured dose receiving means, and means including a plunger connected to said needle and extending along the axis of the inoculator to a position to be manually activated to move said needle from a closed to an inoculating position and spring means coiled about said needle and acting on said plunger to return the needle from its inoculating position to its said closed position.

2. An apparatus according to claim 1 wherein said elongated slot extends through said needle and defines one side opening on each side of the needle.

3. An apparatus according to claim 1 wherein one said side opening is flared about at least a substantial portion of its perimeter 4. An apparatus according to claim 2 wherein of said side openings is flared about its entire perimeter.

5. An apparatus according to claim 2 wherein both of said side openings are flared about their respective perimeters.

6. A serum inoculator of the type used to inoculate birds and the like against diseases and comprising:

a serum holding reservoir having a dispensing hole;

a needle extending through said reservoir along the axis of the inoculator and being reciprocable in said reservoir from a closed position with its pointed end substantially contained in said hole, to an inoculating position with its end projecting an inoculating distance beyond said hole;

said needle having a measured serum dose receiving means at a closely spaced distance from said pointed end, said measured dose receiving means including an elongated slot having a side opening and wherein one end of the slot includes a projection means projecting into the slot for attracting and holding a predetermined measured serum dose within the slot when said dose receiving means is in contact with said reservoir and for releasing the serum into a bird when the pointed end of the needle is inserted therein;

fixed wiper means in said reservoir adjacent said dispensing hole forming with the pointed end of said needle when said needle is in closed position a seal for sealing serum within said reservoir;

said fixed wiper means wiping said needle on each inoculating movement thereof except that of a measured dose contained within said measured dose receiving means, and means including a plunger connected to said needle and extending along the axis of the inoculator to a position to be manually activated to move said needle from a closed to an inoculating position and spring means coiled about said needle and acting on said plunger to return the needle from its inoculating position to its said closed position 7. An apparatus according to claim 6 wherein said elongated slot extends through said needle and defines a cavity having one side opening on each side of the needle 8. An apparatus according to claim 7 wherein said slot includes a projection extending into the cavity at each end thereof.

9. An apparatus according to claim 6 wherein said slot includes edges that are flared about a substantial portion of its perimeter.

10. The apparatus according to claim 7 wherein each of said side openings include edges that are flared about their respective perimeters.

11. A serum inoculator of the type used to inoculate birds and the like against diseases and comprising:

a serum holding reservoir having a dispensing hole;

a needle extending through said reservoir along the axis of the inoculator and being reciprocable in said reservoir from a closed position with its pointed end substantially contained in said hole, to an inoculating position with its end projecting an inoculating distance beyond said hole; said needle having a measured serum dose receiving means at a closely spaced distance from said pointed end including a diametric slot extending through said needle, said slot having flared edges on each side thereof and further including a projection projecting into the slot at each end thereof for assisting in attracting and holding a predetermined measured serum dose within the slot when said dose receiving means is in contact with said reservoir and for releasing the serum into a bird when the pointed end of the needle is inserted therein;

fixed wiper means in said reservoir adjacent said dispensing hole forming with the pointed end of said needle when said needle is in closed position a seal for sealing serum within said reservoir;

said fixed wiper means for wiping said needle on each inoculating movement thereof except that of a measured dose contained within said measured dose receiving means, and means including a plunger connected to said needle and extending along the axis of the inoculator to a position to be manually activated to move said needle from a closed to an inoculating position and spring means coiled about said needle and acting on said plunger to return the needle from its inoculating position to its said closed position.

12. A serum inoculator of the type used to inoculate birds and the like against diseases and comprising:

a serum holding reservoir having a dispensing hole, a needle having a pointed end reciprocable in said reservoir from a closed position with its end substantially contained in said hole to an inoculating position with its end projecting an inoculating distance beyond said hole, having an elongate diametric serum dose receiving slot therein at a closely spaced distance from said end, said slot including flared edges and having projections located proximate each end of said slot for positively attracting and retaining a predetermined measured serum dose within the slot, and an annular sealing element mounted within said reservoir adjacent said hole having an inner periphery adapted to abut said needle as it passes through said hole and to wipe all serum from the surface of said needle on each inoculating movement thereof, except that of a measured dose contained within said diametric slot, and means to reciprocate said needle from a closed to an inoculating position.

13. An apparatus according to claim 12 wherein said serum holding reservoir is transparent.

14. An apparatus according to claim 12 wherein said serum holding reservoir has an externally threaded nipple forming end, the annular wiping washer abuts the end of said nipple and a retaining cap is provided having a bottom wall and a needle hole therein and an annular internally threaded side wall threaded on to said reservoir nipple to compress the outer edge of said wiping washer against the end of said nipple 15. An apparatus according to claim 13 wherein the serum reservoir comprises a cylinder and in which the means to reciprocate the needle within the cylindrical reservoir comprises a plunger reciprocable in a cylinder connected to said cylindrical reservoir.

16. An apparatus according to claim 13 in which the serum reservoir comprises a cylinder and in which the means to reciprocate the needle within the cylindrical reservoir comprises a plunger reciprocable in a cylinder connected to said cylindrical reservoir and in which one end of the cylinder has an internally threaded socket and the other end of the cylindrical reservoir has an externally threaded nipple threaded within said cylinder socket and an annular resilient washer having a central needle hole therein is used by the reservoir nipple against the base of the socket.

17. A serum inoculator according to claim 12 in which the serum reservoir comprises a cylinder and in which the means to reciprocate the needle within the cylindrical reservoir comprises a plunger reciprocable in a cylinder connected to said cylindrical reservoir, and in which the cylinder comprises a barrel of uniform diameter throughout its length and the plunger has a thumb operated manipulating button on the upper end thereof and a finger grip is provided having a hub longitudinally adjustably securable to said barrel and diametric arms each having the same side wall thereof longitudinally grooved to receive a finger, whereby two fingers may be inserted in said grooves and the thumb inserted over the button to correctly align the inoculator for accurate adjustment prior to the thumb manipulation of the plunger and needle.

18. A serum inoculator of the type used to inoculate birds and the like against diseases and including:
a reservoir for serum;
a needle extending within said reservoir and movable with respect thereto having a measured serum dose receiving means near one end thereof, said measured dose receiving means comprising an elongate diametric slot defining one side opening on each side of the needle, said slot having flared sides and further including a projection at one end thereof projecting into the slot for assisting in attracting and holding a predetermined measured serum dose within said slot;
a wiper element held at one end of the reservoir for wiping that portion of the surface of said needle, except for the said measured dose receiving means, which passes through the said element as the needle is moved with respect to said reservoir;
means connected with the other end of said reservoir including a plunger to which said needle is secured and by which the needle can be moved manually in one direction with respect to said reservoir and said wiping element, and
spring means coiled about said needle and acting on said plunger to effect return movement of the needle in the opposite direction 19. A serum inoculator of the type used to inoculate birds and the like against diseases and comprising:
a reservoir for serum;
a reciprocable needle having a portion movable into and out of said reservoir for insertion in and removal from the bird to be inoculated, said needle having in that portion thereof which enters and exits from said reservoir, an elongate diametric slot defining a side opening on each side of the needle, said slot including flared sides and a projection extending into said slot at each end thereof, said slot being adapted to positively attract and hold a predetermined measured serum dose for a single inoculation;
wiping means fixed in position at the dispensing end of said reservoir for removing from said needle the serum other than the serum held within the said elongate diametric slot; and
means connected to said needle and operable thereon for imparting reciprocating strokes thereto for drawing the said portion into the reservoir to charge the elongate diametric slot with serum and to project it therefrom to an exposed position for inoculating use.

* * * * *